(12) United States Patent
Fehlmann et al.

(10) Patent No.: US 10,350,937 B2
(45) Date of Patent: Jul. 16, 2019

(54) APPLICATOR PEN

(71) Applicant: SIKA TECHNOLOGY AG, Baar (CH)

(72) Inventors: Daniel Fehlmann, Uerkheim (CH);
Dana Maiwald, Zürich (CH);
Dominique Burkard, Gretzenbach (CH)

(73) Assignee: SIKA TECHNOLOGY AG, Baar (CH)

( * ) Notice: Subject to any disclaimer, the term of this patent is extended or adjusted under 35 U.S.C. 154(b) by 135 days.

(21) Appl. No.: 15/321,658

(22) PCT Filed: Jul. 16, 2015

(86) PCT No.: PCT/EP2015/066355
§ 371 (c)(1),
(2) Date: Dec. 22, 2016

(87) PCT Pub. No.: WO2016/012353
PCT Pub. Date: Jan. 28, 2016

(65) Prior Publication Data
US 2017/0217244 A1    Aug. 3, 2017

(30) Foreign Application Priority Data

Jul. 25, 2014  (EP) .................................... 14178613
Jul. 25, 2014  (EP) .................................... 14178614

(51) Int. Cl.
*B43K 8/00*       (2006.01)
*B05C 17/00*      (2006.01)
*A61F 13/40*      (2006.01)

(52) U.S. Cl.
CPC ................ *B43K 8/00* (2013.01); *B05C 17/00* (2013.01); *B05C 17/002* (2013.01); *A61M 35/006* (2013.01)

(58) Field of Classification Search
CPC ..................................................... A61M 35/006
(Continued)

(56) References Cited

U.S. PATENT DOCUMENTS 4,304,869 A * 12/1981 Dyke .................. A61M 35/006
                                                          206/219
4,957,385 A    9/1990  Weinstein
(Continued)

FOREIGN PATENT DOCUMENTS

WO    2006/131747 A1    12/2006
WO    2014/004521 A1    1/2014

OTHER PUBLICATIONS

Jan. 31, 2017 International Preliminary Report on Patentability issued in International Patent Application No. PCT/EP2015/066355.
(Continued)

*Primary Examiner* — David J Walczak
*Assistant Examiner* — Joshua R Wiljanen
(74) *Attorney, Agent, or Firm* — Oliff PLC

(57) ABSTRACT

An applicator pen for discharging a liquid onto a surface, preferably for applying a protective layer onto adhesive surfaces of a vehicle, in particularly for improved adhesion in the case of bonding applications, the applicator pen including a hollow body and an ampoule received in the hollow body, including a peripheral surface, for receiving the liquid, wherein the ampoule is able to be broken to enable the liquid to escape, wherein a breakage device is provided with an axially movable portion and is realized in such a manner that a movement of the movable portion in the axial direction results in the breaking of the ampoule.

11 Claims, 10 Drawing Sheets

(58) Field of Classification Search
USPC .............. 401/132, 133; 206/528, 530, 532; 222/81; 604/3
See application file for complete search history.

(56) References Cited

U.S. PATENT DOCUMENTS 6,340,097 B1 * 1/2002 D'Alessio ........... A61M 35/003
                                                               215/12.2
2004/0240927 A1 12/2004 Hoang et al.

OTHER PUBLICATIONS

Dec. 15, 2015 International Search Report issued in International Patent Application No. PCT/EP2015/066355.

* cited by examiner

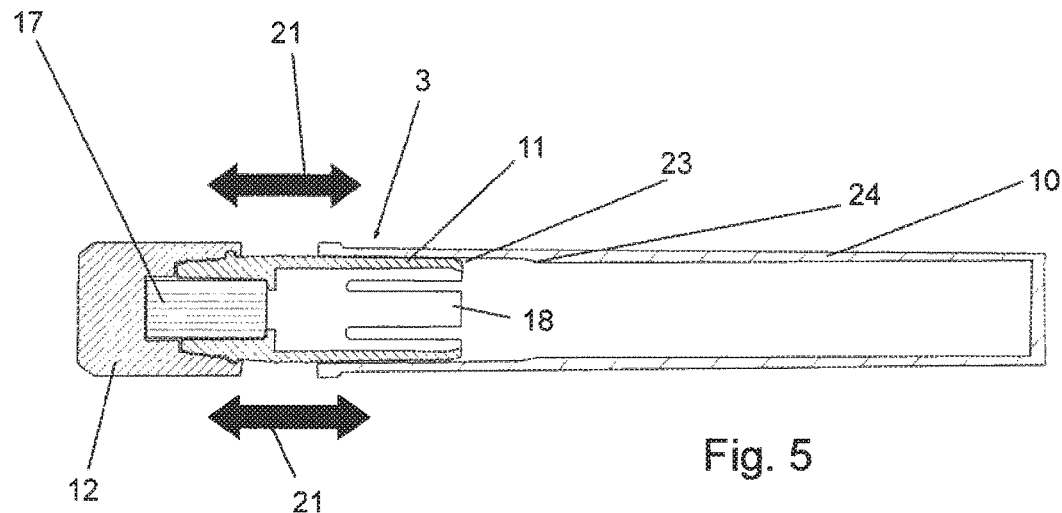
Fig. 5
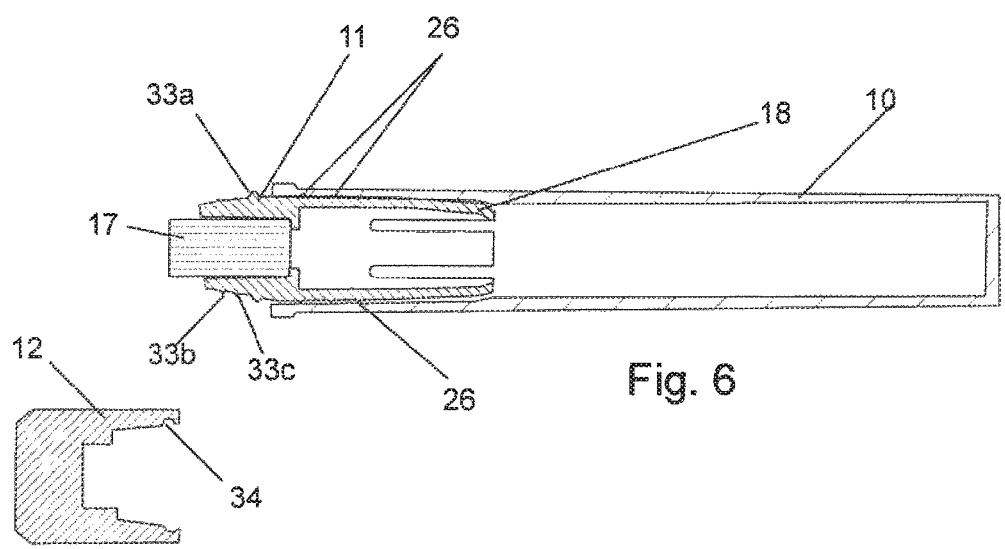
Fig. 6
Fig. 7

APPLICATOR PEN

TECHNICAL SCOPE

The invention relates to an applicator pen for discharging a liquid onto a surface, preferably for applying a protective layer onto adhesive surfaces of a vehicle, in particularly for improved adhesion in the case of bonding applications, said applicator pen including a hollow body in which the liquid is received, preferably inside an ampoule which is received in the hollow body and is able to be broken to enable the liquid to escape.

PRIOR ART

Pre-treatment agents for generating adhesive connections are usually provided in packaging which consists of an aluminum bottle, polyethylene cup and a screw-type closure for the bottle produced from polyethylene. In the area of disposable applications, aluminum tubes or primer pens and activator pads are also each provided with a small amount of contents.

Applicator pens of the above-described type are disclosed, for example, in WO 2014/004521 A1. WO 2014/004521 A1 describes an applicator pen, including a cylindrical body in which a glass ampoule is held, an applicator-part by means of which the liquid can be applied onto a surface as well as a closure cap. The ampoule is destroyed by pressure exerted radially onto the peripheral surface of the applicator-part such that the liquid emerges out of the ampoule. The applicator-part includes a porous body for applying the liquid. A seal between the individual parts (cylindrical base body, applicator-part and cap) is effected by means of a press fit. All in all, in the case of the applicator pen according to WO 2014/004521 A1, there is the risk of the liquid drying making it difficult for said applicator pen to be able to be used multiple times (over a longer period of time). In addition, the type and manner of the breaking of the ampoule is felt to be comparatively complicated and not very "intuitive".

The object consequently underlying the invention is to provide an improved applicator pen of the generic type which is able to be used, in particular, multiple times over a longer period of time and which is able to be operated in a simple manner.

DISCLOSURE OF THE INVENTION

Said object is achieved in particular by an applicator pen with the features of claim 1.

The object is achieved, in particular, by an applicator pen for discharging a liquid onto a surface, preferably for applying a protective layer onto adhesive surfaces of a vehicle, in particularly for improved adhesion in the case of bonding applications, said applicator pen including a hollow body for receiving the liquid, in particular inside an ampoule received in the hollow body (including a peripheral surface), wherein the ampoule is able to be broken to enable the liquid to escape.

According to a first independent aspect, a breakage device with an axially movable portion is provided and realized in such a manner that a movement of the movable portion in the axial direction results in the breaking of the ampoule. As a result, an easily intuitively intelligible possibility for breaking the ampoule is created that is simple as well as effective. The prior art proposes breakage devices which require a force to be applied radially (for example as a result of bending against a table edge or pressing-in a peripheral surface), which is perceived as comparatively time-consuming and complicated. A breakage of the ampoule can be achieved in a comparably simple manner, however, according to the invention, by means of the effect of an axial force (for example as a result of an impact against an end of the applicator pen or of a rotational drive by means of a thread, as explained in more detail below). An "axial" movement or application of force is to be understood as a movement or application of force in the direction of the longitudinal axis of the applicator pen.

According to a second, independent aspect (which can preferably be combined with the first aspect), the hollow body comprises at least two parts, preferably at least three parts, wherein a sealing ring, in particular a sealing lip, is provided on at least one surface, in particular a peripheral surface, of one of the parts which faces a surface, in particular a peripheral surface, of a further part. The sealing ring, in particular the sealing lip, is preferably integrally formed on one of the facing surfaces. A "sealing ring" is to provide a structure which is closed per se. A "sealing lip" is preferably a "sealing ring" which is realized as a ring lamella. A core concept of the second aspect consists in providing at least one sealing ring which simplifies sealing of the individual parts of the applicator pen. In particular, when the individual parts are movable (as, for example, a closure cap in relation to a head part or a head part in relation to a base part, for example for breaking the ampoule), a high degree of tightness is made possible with at the same time a comparatively simple relative movement.

All in all, more than one sealing ring, for example at least two, preferably at least three or four sealing rings (sealing lips) can be provided on one of the facing surfaces. Several sealing rings (sealing lips) can be provided, for example, on an outer peripheral surface, a first group of sealing rings facing an inside surface of a closure cap and a second group of sealing rings facing an inside peripheral surface of a base part.

According to a third, independent aspect of the invention (which can preferably be combined with the first and/or second aspect), the hollow body includes at least one closure cap as well as one base body which preferably includes an end of the applicator pen remote from the closure cap, wherein the closure cap includes a liquid-applicator part (in particular a liquid-applicator felt), wherein the closure cap can be removed from the base part together with the liquid-applicator part, wherein, with the closure part in the removed state, the liquid-applicator part can be placed onto the surface onto which liquid is to be applied, for applying the liquid. A core concept of the third aspect consists in that a liquid-applicator part is arranged inside the closure cap and the closure cap consequently serves at the same time as a device for applying the liquid. In the prior art, for example WO 2014/004521 A1, the liquid-applicator part remains in the main body of the pen. The result of this is that when the liquid-applicator part dries, either the entire applicator pen has to be thrown away or, (if this is even possible), the liquid-applicator part has to be removed as such from the applicator pen, which is linked to a corresponding contamination hazard for the user. In contrast, the invention according to the third aspect makes it possible for the cap including the liquid-applicator part to be replaced in its entirety. As the cap is only a relatively small or a simply producible component, it is only linked with low costs and with a low effect on the environment. This results, in general, in the applicator pen being able to be used several times within a longer period of time.

According to a fourth, independent aspect of the invention (which can preferably be combined with the first and/or second aspect and/or third aspect), the hollow body comprises at least one base body and one head part, wherein the head part includes a (flexible) end surface with a slot. The slot can comprise a width of no more than 1 mm, preferably 0.5 mm, even further preferably no more than 0.2 mm. In addition, the slot can comprise a length of at least 1.5 mm, preferably at least 2 mm or no more than 10 mm, preferably no more than 5 mm. A core concept of the fourth aspect consists in showing an application possibility according to the "baby bottle principle". In addition, a, where applicable transparent, closure cap can be provided. The head part can be produced from a (soft) plastics material, for example polyolefin (e.g. polyethylene and/or polypropylene) or from silicone. The head part is preferably realized such that it can be pressed-in in its front region such that the liquid is able to be metered and applied as a result. The head part preferably does not comprise any felt and is realized in a "felt-less" manner.

The ampoule is able to be broken open in a more secure manner as a result. In particular, it has been recognized that fragments of the ampoule cannot (or at least are less likely to) move out of the applicator pen in the case of such a method of operation.

In a preferred development, the movable portion is arranged and realized in such a manner that it can be moved in the axial direction as a result of an impact onto an end of the applicator pen carried out in the axial direction such that the ampoule breaks. The "impact" can be directed, for example, onto an end of the applicator pen which is located opposite the outlet region. However, the "impact" preferably occurs onto an end at which the outlet region is arranged, for example onto a closure cap or a head part. An "impact" is to be understood, in particular, as a preferably short-term compressive stress, e.g. lasting for less than 0.1 s.

In an alternative further development, the movable portion can be driven as a result of rotation of a rotatable portion, in particular a closure cap, such that a rotation of the rotatable portion drives the movable portion in the axial direction such that the ampoule breaks. The rotatable portion can be realized by the movable portion itself (at least in part). A corresponding rotary drive can be realized, for example, by a thread (screw thread). When the user then turns the movable portion (or a rotatable portion of the applicator pen which is operatively connected to the movable portion), the movable portion is at the same time driven in the axial direction until the ampoule breaks. It is particularly preferred, in this context, when it is also possible to remove a closure cap from the remaining components of the applicator pen by means of the same thread. For example, the movable portion (e.g. a head part) can be connected to the closure cap (operatively connected). By means of rotating the closure cap, the movable portion can then be moved in the axial direction toward the ampoule such that said ampoule breaks. Once the ampoule has been broken, the closure cap can then be rotated in the opposite direction such that the closure cap can be removed from the remaining component parts of the applicator pen. All in all, these types of measures demonstrate a simple possibility for breaking the ampoule which can be carried out without a lot of effort.

It is advantageous also in the case of said further development when one end which includes the outlet region and/or a portion which includes the head part is rotated such that it is moved in the direction of the base part; the force that finally breaks the ampoule therefore acts from the end of the applicator pen with the outlet region. This increases safety when breaking open the ampoule.

The breakage device preferably includes a diverting device in such a manner that a force, which acts axially on account of the movement of the movable portion, is diverted in the direction of the peripheral surface of the ampoule (to break the ampoule). In the case of this type of embodiment, on the one hand, therefore, it is possible to break the ampoule by means of an axial movement (for example an impact from the front or the rear) and this is combined in a synergetic manner with the fact that by means of the diverting device a force acting on account of the axial movement is directed onto the peripheral surface of the ampoule such that the ampoule is able to be destroyed with comparatively little force expenditure.

In a specific embodiment, the breakage device comprises at least one (preferably pliable) claw, preferably in such a manner that the at least one claw is driven against the peripheral surface of the ampoule by the axial movement of the movable portion. As a result of a claw of this type, it is possible to break the ampoule with a comparatively low force expenditure, which improves the operability of the applicator pen.

The at least one claw can comprise a run-up inclination such that the claw (for example when running up against a corresponding run-up inclination or a stop) can be driven against the ampoule and breaks said ampoule.

When several claws are provided, they are preferably spaced apart from one another by means of slots. Said slots preferably have (on average) a smaller diameter in a direction perpendicular to the axial direction than the claws (on average). For example, the claws can be (on average) at least 1.5 times, preferably at least 2 time as wide (in the direction perpendicular to the axial direction) as the slots (on average). As a result, the ampoule can be both securely guided and held at least in phases by the claws and broken in a controlled manner.

A (distal) end or an end of the claw which comes into contact with the ampoule during the breaking operation, can be curved inward or can comprise a projection which points radially inward. As a result, the claw "hammers" onto the ampoule such that said ampoule breaks in a controlled and efficient manner. In general, a "claw" can be understood as a structure which extends in part in an (inwardly) curved manner.

In a specific embodiment, two claws are arranged located opposite one another. As an alternative to this or in addition to it, two guide portions can be arranged next to the claws in the peripheral direction. Said guide portions can comprise axially extending ribs which can guide and hold the ampoule for controlled and reliable breaking. Said guide portions are also located opposite one another. All in all, a first guide portion, a first claw, a second guide portion and a second claw can therefore be arranged in said order in the peripheral direction. Slots, which comprise, for example, a diameter which is smaller than the diameter of the claws and/or of the guide portions (in the peripheral direction), are situated between said four elements.

Ring portions, which can have an at least partially sealing function, can be provided on an outer peripheral surface of the at least one claw (and/or of the guide portion).

The claw is preferably an (in particular integral) component part of a (the) head. A free end of the claw preferably points in the direction of a rear end of the applicator pen (for example in the direction of a base part). As a result, the ampoule is able to be broken in a secure and efficient manner.

The hollow body preferably comprises a head part and a base body which includes an end remote from the outlet region. The head part is preferably movable in the axial direction in relation to the base body. In said embodiment, the head part can define the movable portion or can realize at least part of the movable portion. In addition, the head part can realize at least one component part of the breakage device.

In a specific development, the head part is guided at least in portions inside the base body. In a preferred development, the head part can comprise the above-described claw. The head part can be realized in a cylinder-shaped manner (just as the base body) at least in portions. In particular, when a relative movement between the head part and the base body is utilized in order to break the ampoule (e.g. when an axial impact is present), the operability of the applicator pen is improved.

In one embodiment, a head part (in particular the above-described head part) comprises at least one (porous) liquid absorption body, in particular at least one absorption sponge and/or one liquid-applicator felt for applying the liquid. In the case of said embodiment, for example a closure cap is removed from the unit of base body and head part such that a liquid-applicator felt (in particular the liquid-applicator felt) is outwardly accessible for applying the liquid. The absorption sponge can ensure that vibrations are absorbed during transport and the ampoule is protected as a result. In addition, it can ensure that when the ampoule is broken no glass splinters emerge in the front region. All in all, operability is simplified and injuries prevented as a result.

The hollow body (in particular a base body of the hollow body) preferably comprises at least one run-up inclination on an inner peripheral surface in such a manner that an axially acting force is converted, at least in part, into a radially inwardly directed force (directed onto the outer peripheral surface of the ampoule). The run-up inclination preferably interacts with the claws described further above. Said claws, in turn, can also comprise a corresponding run-up inclination. All in all, a preferred embodiment is developed such that a run-up inclination of a claw interacts with a run-up inclination of the base such that an axial displacement of the claw in the direction of a rear end of the applicator pen forces the claw radially inward such that it presses against the ampoule and breaks it. This demonstrates overall, as a result, a structurally simple solution to break the ampoule in a reliable manner.

In a specific embodiment, a (removable) film element, in particular a label, can be arranged around the applicator pen. The film element can preferably be arranged about a/the head part and/or between a/the closure cap and a/the base body. The film element can be realized such that it blocks an axial movement between the head part and the base body such that—insofar as the film element is attached the ampoule cannot be broken. In the case of a specific application, the film element is then removed, as a result of which the blocking by the film element is eliminated and the ampoule is able to be broken. If, for example, the film element (label) is correspondingly inscribed, intuitive and simple operation of the applicator pen can be achieved.

In general, the hollow body can comprise different parts, in particular a base body, preferably including an end of the applicator pen remote from the outlet region and/or a head part (for example adjoining the base body) and/or a closure cap.

A liquid-applicator part (in particular a liquid-applicator felt) and/or a sponge (absorption sponge), which prevents glass splinters of the ampoule from passing to the outside, can be arranged as component parts of the applicator pen inside the hollow body.

The liquid-applicator part, in particular the liquid-applicator felt can protrude at least in part from the closure cap, in particular by at least 2 mm or at least 4 mm. As a result, the liquid-applicator part, in particular the liquid-applicator felt is simply accessible from the outside such that liquid can be applied onto a surface.

The liquid-applicator part can be connected, in particular pushed-in and/or pressed-in and/or bonded and/or welded, to the cap (where applicable in a fixed and/or integral manner).

An end of the closure cap remote from the liquid-applicator part can comprise a recess. Said recess comprises, for example, a diameter of at least 0.5 cm and/or no more than 1 cm and can comprise, for example, a round cross section. As a result of such a recess, the closure cap is able to be gripped in a particularly simple manner such that the closure cap can be removed in a simple manner and, in particular, can function in a simple manner as a device for applying the liquid (by way of an integrated liquid-applicator part). Operability is improved as a result.

The closure cap can comprise axially extending ribs on its outer peripheral surface. This also improves the operability of the cap, in particular when said cap functions as a device for applying the liquid (with an integrated liquid-applicator part).

According to an independent aspect of the invention, a closure cap is proposed for an applicator pen, in particular of the afore-described type, wherein the closure cap comprises an, in particular porous liquid-applicator part, preferably a liquid-applicator felt.

At least one sealing ring (sealing lip) can comprise at least one interruption, in particular a notch, wherein the interruption (notch) is preferably shorter than 3 mm, in particular shorter than 1.5 m. The notch can be longer than 0.3 mm, in particular longer than 0.7 mm. Several sealing rings (arranged one behind another in the axial direction) are preferably provided (in particular in the case of said further development). At least one first sealing ring can be provided without interruption. At least one second sealing ring can comprise at least one interruption (notch). According to a general concept, an arbitrary sealing element can be present which comprises an interruption (recess or channel) in such a manner that, when a part (head part) which includes an applicator-part (e.g. felt) and a base part in which a liquid (primer) is situated are moved toward one another, air is able to escape (or is able to escape at least in part) through said interruption (recess or channel). Insofar as a "sealing ring" is mentioned here and below, this can be replaced by a general "sealing element". All further developments of the sealing ring (which do not relate directly to the ring geometry) are then also applicable to such a "sealing element".

In a specific embodiment, precisely one first sealing ring is provided as well as (precisely) two second sealing rings. The at least one first sealing ring can be arranged in a distal manner in relation to the at least one second sealing ring. A "distal" arrangement is to be understood as an arrangement where the corresponding sealing ring is arranged closer to a head end or further away from a rear end of the applicator pen. The interruptions (notches) can be (approximately) U-shaped or V-shaped.

Insofar as the length of the interruption (notch) is specified, it is to be understood, in particular, as the length of the interruption (notch) in the peripheral direction (that is to say along an imaginary line which the sealing ring would follow were it not to have an interruption).

At least one sealing ring can comprise at least two or at least three interruptions (notches). Insofar as more than one sealing ring with at least one interruption is provided, the interruptions of the several sealing rings can be aligned with one another (in the axial direction). As a result, air can escape in a particularly effective manner. The respective sealing ring can comprise a height (in the radial direction) of at least 0.4 mm, in particular at least 0.6 mm and/or no more than 2.0 mm, in particular no more than 1.2 mm. Insofar as details are not specified further above or below, each sealing ring can basically be realized (extend) in a non-interrupted manner or also comprise one or several interruptions (notches).

All in all, overpressure, which is generated when parts of the applicator pen that are displaceable (movable) in relation to one another are modified as regards their relative position with respect to one another, can be reduced as a result of the above-described interruptions (notches) inside the sealing rings. In the case of such a displacement (movement), overpressure can namely be generated which is relieved by the interruptions (notches). For example, when a (the) head part is pressed into the interior of the applicator pen (or against an ampoule or in the direction of the rear end of the applicator pen), overpressure can occur in the interior of the applicator pen such that (with the applicator pen in the corresponding position) contents leak out. Installing interruptions (leakage openings) in particular on "inner" (proximal) sealing rings prevents or reduces at least said problem as the (pressurized) air is able to escape at least for the most part. Insofar as a (small) overpressure remains, this is even advantageous under certain circumstances as it promotes the filling of an applicator-part (felt). Without such a (small) overpressure, the filling of the applicator-part (felt) can last some time (where applicable significantly longer).

In a specific embodiment, at least one sealing ring (sealing lip) comprises precisely two interruptions (notches) such that, air, when individual components are moved toward one another (for example when the head part and the base part are moved toward one another), in particular when screwing two components together (in particular the head part and the base part), is able to escape (at least) until a further additional sealing lip which is present, where applicable (without interruptions or notches), realizes a seal (for example when said additional sealing lip is provided on the head part, when said sealing lip provided there comes into contact with the base part). All in all, (defined) overpressure is generated which ensures that, when the ampoule is opened (broken) and where applicable a closure is removed, the contents (primer) rapidly fill an applicator-part (felt).

DESCRIPTION OF THE DRAWINGS

Advantages and expediency of the invention become clear from the following description of preferred exemplary embodiments by way of the figures, in which:

FIG. 5 shows a schematic section view of a second embodiment of the invention;

FIG. 6 shows a schematic section of the embodiment according to FIG. 5 in a modified position without a cap;

FIG. 7 shows a schematic section of the cap according to the embodiments according to FIGS. 5 and 6;

FIG. 1 shows a schematic section of a first embodiment of an applicator pen. The applicator pen includes a base body 10, an (axially movable) head part 11 (which forms a movable portion) as well as a closure cap 12. The base body 10, head part 11 and closure cap 12 define a hollow body 3. The base body 10 comprises an end 14 (rear end) of the applicator pen remote from an outlet region 13. An ampoule 15 (shown by the broken line) is arranged in the hollow body 13, specifically inside the base body 10 and (in part) inside the head part 11. A sponge 16, which prevents the ampoule (or splinters thereof) being able to fall out of the applicator pen, is additionally provided. The sponge 16 is provided inside the head part 11. A liquid-applicator felt 17 is arranged according to FIG. 1 in part inside the head part 11 and the closure cap 12. The ampoule 15 can be broken by means of claws 18 (four claws are provided in the present example, but said number is not compulsory) such that liquid emerges out of the ampoule.

The breaking of the ampoule is illustrated in particular in FIGS. 2 and 3. FIGS. 2 and 3 show an enlarged detail from the embodiment according to FIG. 1 in a first position (FIG. 2) and a second position (FIG. 3). It can be seen in FIG. 2 that a stop 19 of the head part 11 is removed from a stop 20 of the base body 10 such that the head part 11 and the base body 10 are able to be moved toward one another, which is symbolized by the arrows 21. If an impact is then exerted in the direction of the arrows 21 onto an end 22 of the applicator pen which is assigned to the outlet region 13 and in the present case is formed by the closure cap 12, the head part 11 including the cap 12 is displaced in the direction of the base body 10. The end state is shown in FIG. 3. During said movement, run-up inclinations 23 of the claws 18 come into contact with an (annularly peripheral) run-up inclination 24 of an inside peripheral surface of the base body such that the (flexible) claws are bent inward (in the radial direction)

Figure 3:
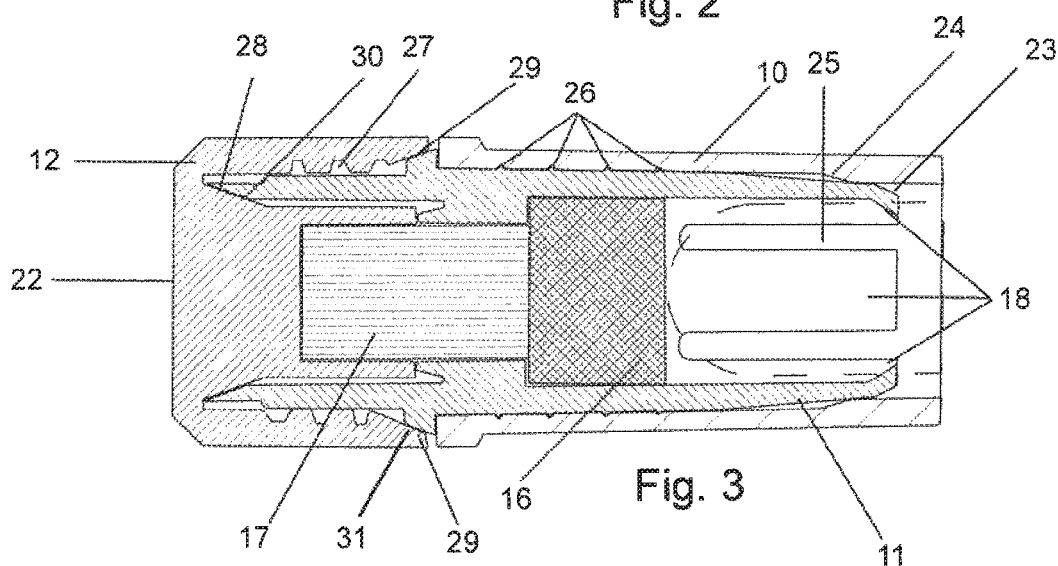
FIG. 3 shows the detail according to FIG. 2 in a modified position.

such that pressure is exerted onto the ampoule and said ampoule breaks (see FIG. 3). The impact necessary for breaking the ampoule can be effected, for example, as a result of the base body 10 being gripped and the cap 12 being knocked (hit) frontally against a wall.

In order to make it easier for the claws 18 to be able to bend radially inward, they are spaced apart from one another by means of slots 25.

Sealing between the base body 10 and the head part 11 (see FIG. 3) is effected by means of sealing rings 26 which are provided on an outer peripheral surface of the head part 11 which is situated opposite an inner peripheral surface of the base body 10. As a result of said sealing rings 26, a high level of tightness is achieved without the mobility between the head part 11 and the base body 10, which is necessary for breaking the ampoule, having been excessively restricted. The cap 12 can be screwed onto the head part 11 by means of a screw thread 27 (the associated thread of the head part is not to be seen in the figure as it is realized in an interrupted manner and the interruptions are in the section plane). The closure cap 12 is sealed in relation to the head part 10 by a cone portion 28 on the closure cap 12 as well as a cone portion 29 on the head part 11. In addition, the head part 11 comprises an annular slanting surface 30, which corresponds with the cone portion 28 of the closure cap 12. In a similar manner, the cap 12 includes an annular slanting surface 31 which corresponds with the cone portion 29 of the head part 11. All in all, reliable sealing of the head part 11 in relation to the cap 12 is realized as a result.

Figure 4:
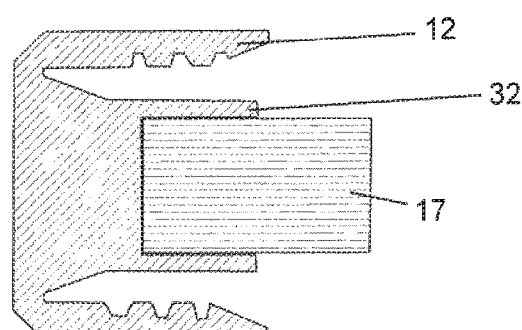
FIG. 4 shows a schematic sectional view of a closure cap of the embodiment according to FIG. 1.

FIG. 4 shows the cap 12 without the head part 11 or the base body 10. As can be seen in FIG. 4, the liquid-applicator felt 17 is arranged in a recess 32 of the cap (for example bonded or welded or integrally formed in another manner; where applicable, the liquid-applicator felt 17 can also be removable from the cap). If, therefore, the cap 12 is removed from the remaining components of the applicator pen, the cap 12 still comprises the liquid-applicator felt 17 which is associated therewith and is saturated with liquid on account of its prior contact with the sponge 16. Said liquid in the liquid-applicator felt 17 can then be applied onto a surface. If the liquid-applicator felt 17 has dried out or is no longer usable for another reason, the cap 12 can be thrown way and replaced by a new cap 12. In this case, the remaining components of the applicator pen can continue to be used. This increases the service life of the applicator pen.

Figure 1:
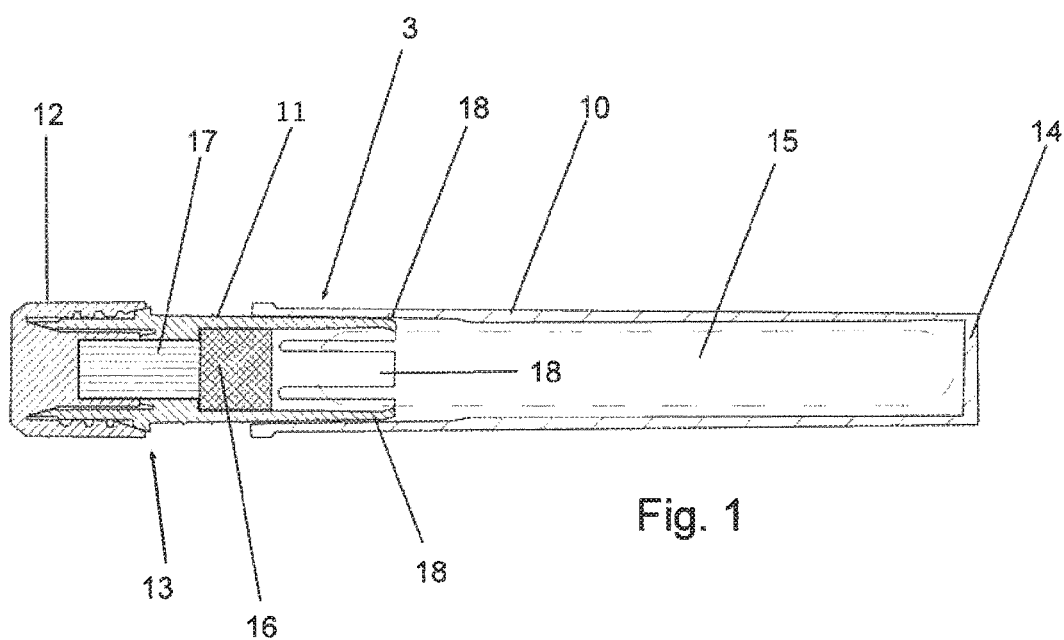
FIG. 1 shows a schematic sectional view of a first embodiment.

FIG. 5 shows a schematic sectional view of a second embodiment of the invention (in a first position). FIG. 6 shows the embodiment according to FIG. 5 without the closure cap. The ampoule is not shown in FIGS. 5 and 6 for reasons of simplicity, but is arranged in a manner analogous to FIG. 1. The mechanism for breaking the ampoule corresponds to the mechanism according to FIGS. 1 to 4 and will not be explained again here. In contrast to the embodiment according to FIGS. 1 to 4, a sponge is not provided in the embodiment according to FIGS. 5 to 7. In the embodiment according to FIGS. 5 to 7, the liquid-applicator felt 17 prevents glass splinters from the ampoule from being able to come out. To this end, unlike in the embodiment according to FIGS. 1 to 4, the liquid-applicator felt 17 (cf. FIGS. 6 and 7) is not integrated in the cap 12 but in the head part 11. Analogous to the embodiment according to FIGS. 1 to 4, the head part 11 is sealed in relation to the base body 10 by sealing rings 26. Said sealing rings 26 can be realized as sealing lips or sealing lamellae. In addition, an outer peripheral surface of the head part 11, which is located opposite an inner peripheral surface of the cap 12, comprises sealing rings 33a to 33c. The sealing ring 33a (see FIG. 7) engages in a corresponding annular recess (groove) 34 on an inner peripheral surface of the cap 12 for realizing a latching connection. The sealing rings 33b, 33c are realized as sealing lips (sealing lamellae) which further improve the sealing. The cap 12 according to the embodiment according to FIGS. 5 to 7 is placed onto the head part 11, a connection being realized as a result of latching-in.

Figure 8:
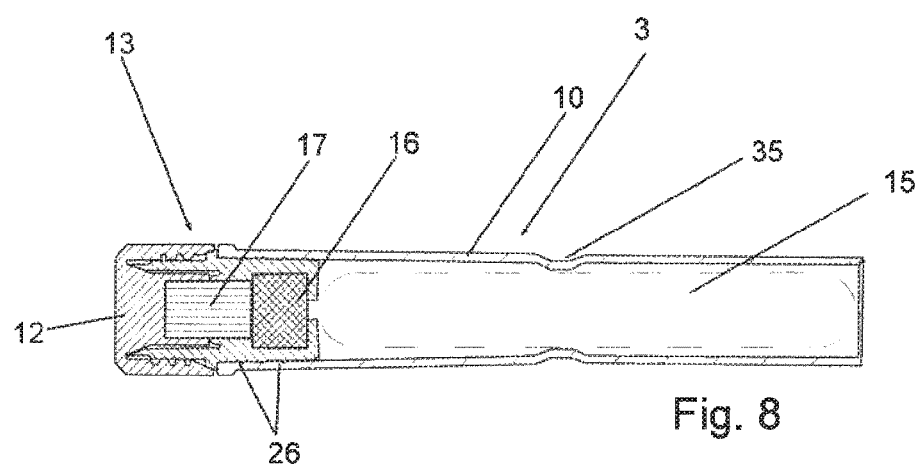
FIG. 8 shows a sectional representation of a third embodiment of the invention.
Figure 9:
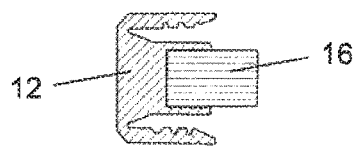
FIG. 9 shows a schematic sectional view of a cap according to the embodiment according to FIG. 8.

FIG. 8 shows a schematic sectional view of a third embodiment of the applicator pen. The third embodiment according to FIGS. 8 and 9 corresponds to the first embodiment according to FIGS. 1 to 4 (in particular with regard to the seal between the head part 11 and the base body 10 or the head part 11 and the closure cap 12 as well as with regard to the liquid-applicator felt 17 and the sponge 16) with the following differences. In the case of the embodiment according to FIGS. 8 and 9, the ampoule 15 is broken by means of an annular constriction which provides a predetermined bending point. On account of the annular constriction 35, the base body 10 can be bent such that the ampoule 15 breaks. As can be seen in FIG. 9, in the case of the third embodiment, analogous to FIG. 4, the liquid-applicator felt 17 is arranged inside the closure cap 12.

Figure 10:
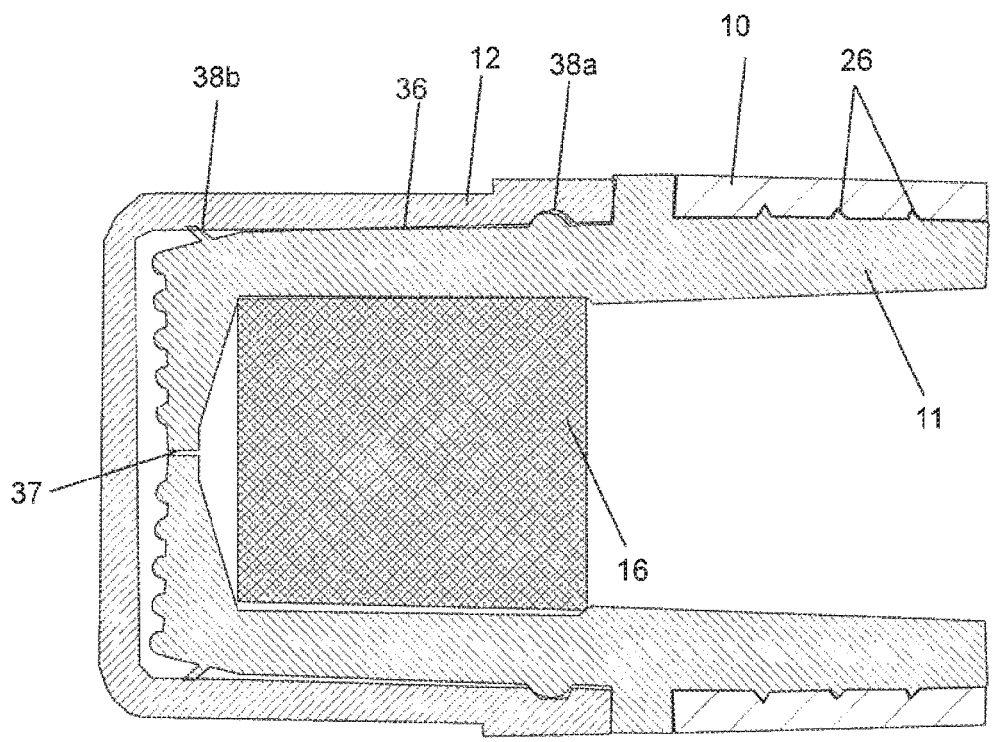
FIG. 10 shows a schematic section of a detail of a fourth embodiment of the invention.
Figure 11:
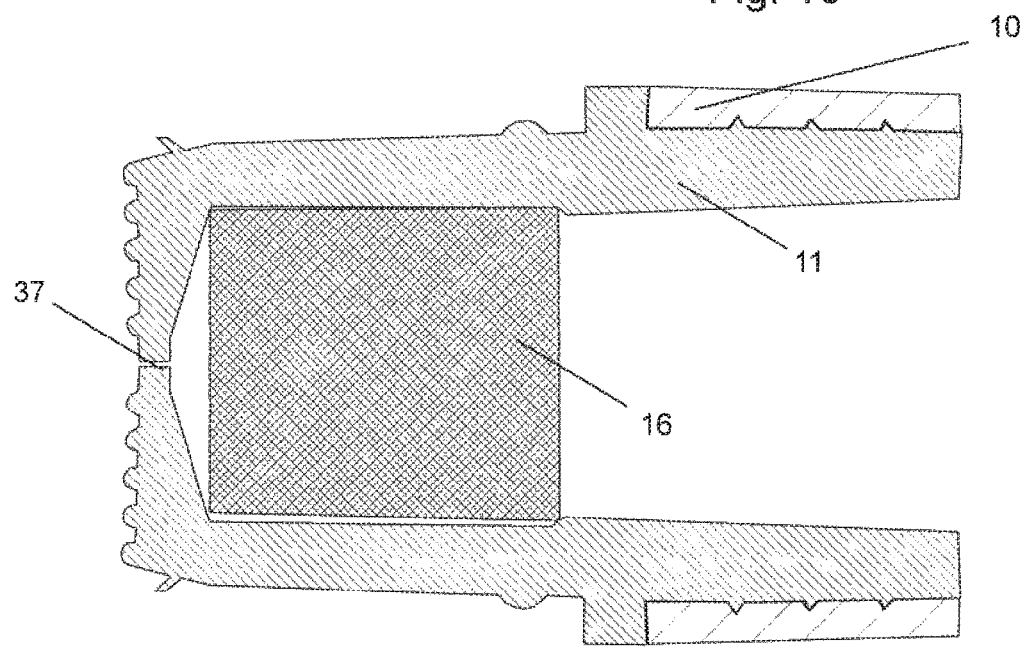
FIG. 11 shows the detail of the embodiment according to FIG. 10 without a closure cap.

FIGS. 10 and 11 show a schematic sectional view of a detail of a fourth embodiment of the invention. The non-shown parts of the fourth embodiment, in particular insofar as this relate to the base body 10 and to the mechanism of breaking the ampoule, can be realized as in the first, second or third embodiment (or in a combination of said embodiments). In contrast to the preceding embodiments, no liquid-applicator felt is provided in the embodiment according to FIGS. 10 and 11. The sponge 16, which additionally sucks up and absorbs liquid, prevents splinters of ampoule from falling out. In order to be able to use the applicator pen according to FIGS. 10 and 11, first of all the (preferably transparent) cap 12 has to be removed (see FIG. 11). As a result of pressing onto a peripheral surface 36 of the head part 11 in the region of the sponge 16, liquid is expelled through a slot 37 according to the "baby bottle principle". Sealing between the head part 11 and the base body 12 is effected by means of sealing lips 26, as in the embodiment according to FIGS. 1 to 4. The cap 12 is sealed in relation to the head part 11 by means of sealing rings 38a, 38b, the sealing ring 38a engaging in a corresponding annular groove 39 on an inner peripheral surface of the cap 12 for realizing a latching connection. The sealing ring 38b is realized as a protruding sealing lamella.

Figure 12:
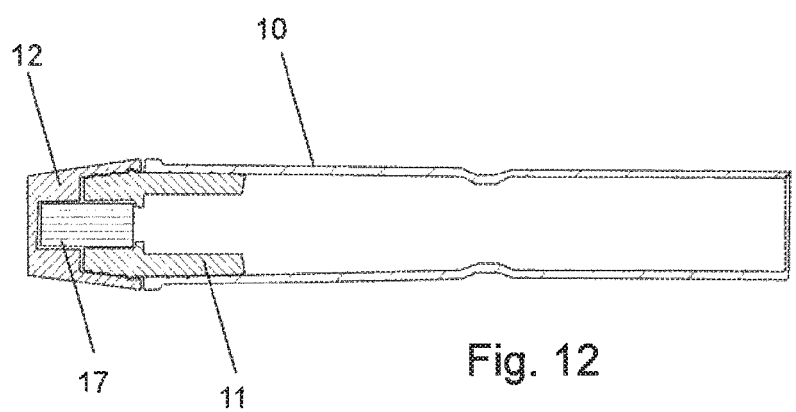
FIG. 12 shows a schematic section of a fifth embodiment of the invention.
Figure 13:
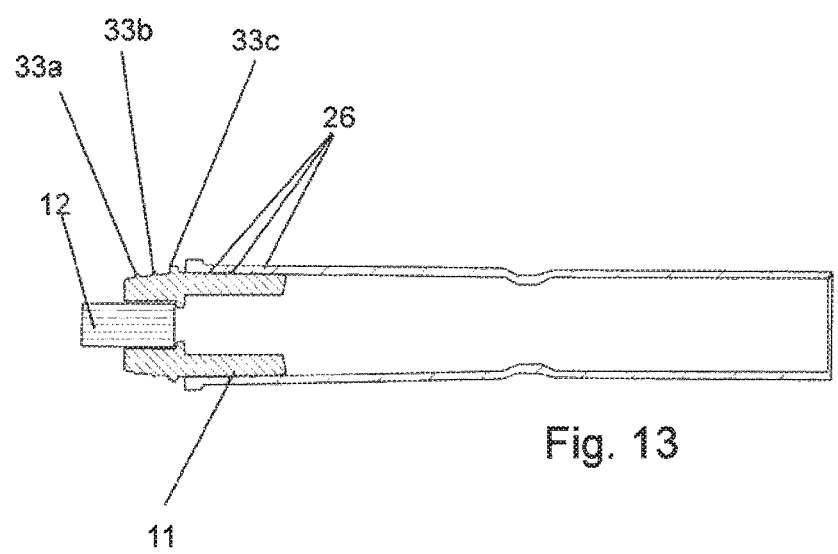
FIG. 13 shows the embodiment according to FIG. 12 without a closure cap.

FIGS. 12 and 13 show sectional views of a fifth embodiment of the invention (FIG. 12 with the closure cap; FIG. 13 without the closure cap). The mechanism of breaking the ampoule corresponds to the mechanism as is described in the case of the embodiment according to FIGS. 8 and 9. A sponge is not provided, but rather a liquid-applicator felt 17. This remains, analogous to the embodiment according to FIGS. 5 and 6, in the head part 11, which comprises sealing lips 26, analogous to the preceding embodiments, in order to realize sealing between the base body 10 and the head part 11. In addition, analogous to the embodiment according to FIGS. 5 to 7, sealing rings 33a to 33c are provided in order to be able to latch-in the closure cap 12 as well as to provide sealing between the closure cap 12 and the head part 11.

Figure 2:
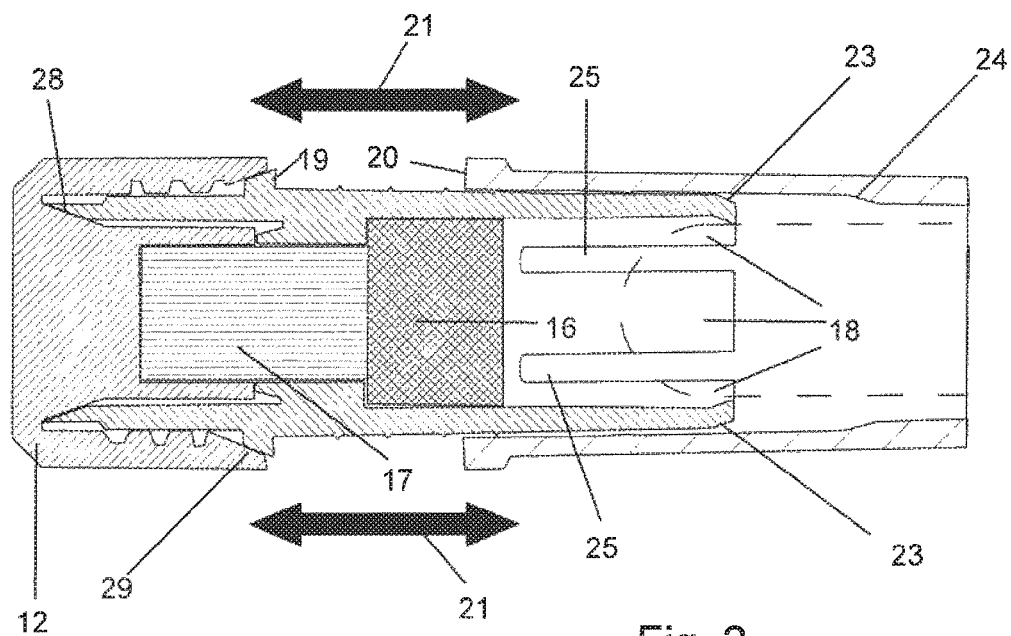
FIG. 2 shows a sectional view of an enlarged detail from the embodiment according to FIG. 1.

In the embodiment according to FIGS. 1 to 4 as well as 5 to 7, a peripheral film element (not shown) can be arranged preferably as a label in a region between the stops 19 and 20 (see FIG. 2). If said label is removed, the stops 19 and 20 are able to be moved toward one another.

In principle, in the case of all the embodiments (where appliable with structural adaptation), the respective cap 12 can be screwed or placed (positioned) onto the head part 11.

The sponge 16 can be, for example, a melamine sponge or can be produced from another plastics material. Generally speaking, the sponge 16 can be formed from a foam material. The ampoule 15 can consist, for example, of glass. The base body and/or the head part and/or the closure cap 12 can be formed from a plastics material, for example polyamide, polyethylene or polypropylene (polyolefin in general).

In principle, the applicator pen is considered for applying liquids onto all types of surfaces. A preferred application is applying a liquid as an adhesion-promoting substrate or as a protective layer in the region of connection surfaces (for example when inserting glazing in the automotive sector).

In general, the liquid-applicator felt 17 can be an arbitrary liquid-applicator part. The liquid-applicator felt can consist of randomly arranged fibers or can consist of fibers aligned in the direction of the fluid.

Figure 14:
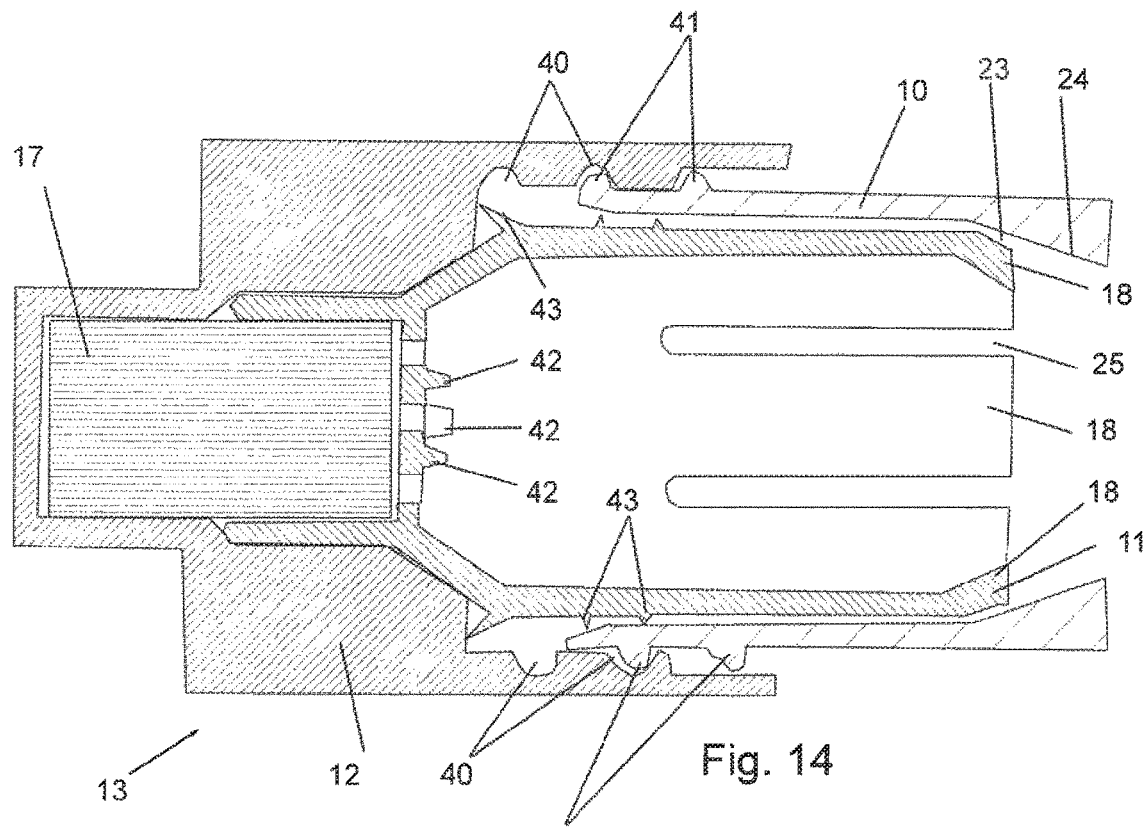
FIG. 14 shows a schematic section analogous to FIG. 2 of a detail of a sixth embodiment of the invention.
Figure 15:
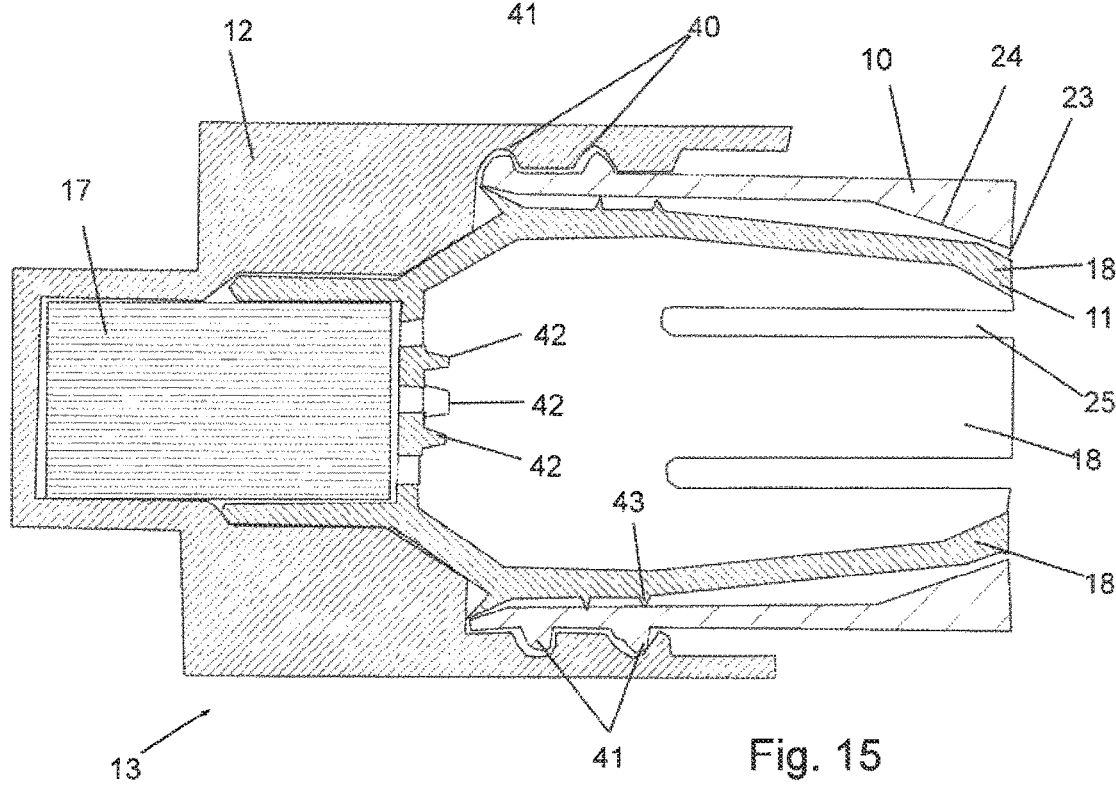
FIG. 15 shows a schematic section analogous to FIG. 3 of a detail of the embodiment according to FIG. 14.

FIGS. 14 and 15 each show a detail of a sixth embodiment of the applicator pen. FIG. 14, in this case, shows a detail analogous to FIG. 2. FIG. 15 shows a detail analogous to FIG. 3. In contrast to the embodiment according to FIGS. 2 and 3, the head part (the movable portion) 11 is not moved by means of an axially acting impact, but as a result of rotating the cap 12. To this end, the cap 12 comprises a thread 40 (which is preferably realized as an internal thread). The base body 10 comprises a corresponding thread 41 (which is preferably realized as an external thread) such that the closure cap 12 is able to be moved as a result of rotation in the direction of the base body 10. As a result, the head part 11 is also urged in the direction of the base body 10 such that the run-up inclination 23 of the head part 11, analogous to the embodiment of FIGS. 2 and 3, runs up against the run-up inclination 24 of the base body 10 such that the claws 18 are pressed inward and an ampoule located between the claws 18 (not shown in FIG. 14 or 15; cf. FIG. 1 for example) breaks. In addition, in the embodiment according to FIGS. 14 and 15, positioning journals 42 are still provided between the liquid-applicator felt 17 and the ampoule (not shown in FIG. 14 or 15) such that the ampoule is able to be positioned and supported before it is broken. Moreover, sealing rings (or sealing lips) 43 are provided between the head part 11 and the base body 10.

Figure 16:
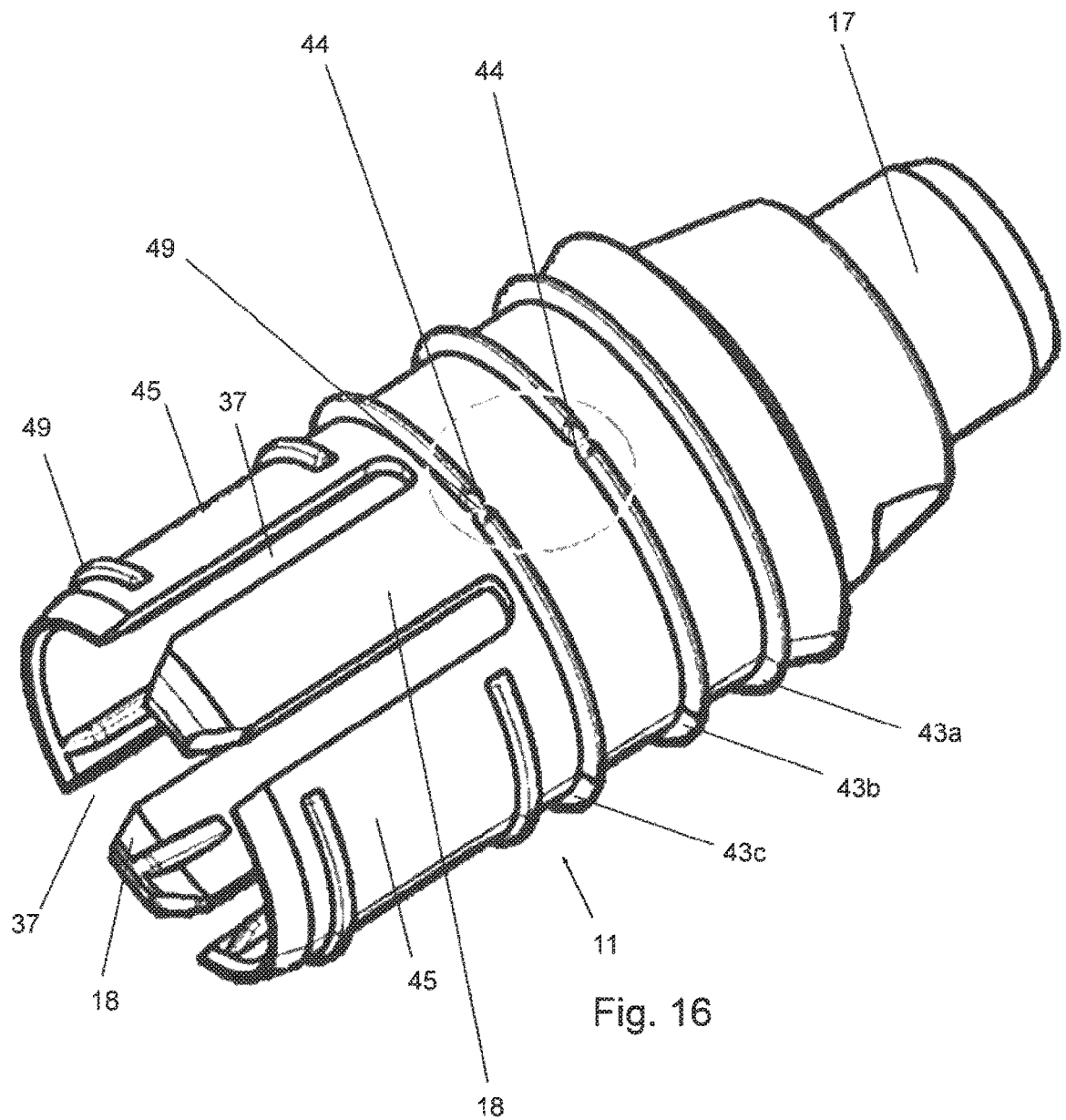
FIG. 16 shows an oblique view of an alternative embodiment of a head part.

FIG. 16 shows an oblique view of a head part 11 according to an alternative embodiment. High-lighted by a circle are notches 44 which are arranged inside "second" sealing rings 43b and 43c. Said sealing rings 43b, 43c extend around the head part without interruptions (with the exception of notches 44, for example two notches 44, one each of which can be seen in the oblique view according to FIG. 16). A "first sealing ring 43a" is realized completely without interruptions. The first sealing ring 43a is arranged closer to a head end (liquid-applicator part) than the sealing rings 43b, 43c, that is to say distally in relation to the sealing rings 43b, 43c. In addition, the embodiment of the head part according to FIG. 16 comprises two claws 18 (located opposite one another). Guide elements 45, which are also located opposite one another, are situated in the peripheral direction between the claws 18. (A total of four) slots 37 are situated between the guide elements 45 and the claws 48. The circular arc sections defined by the slots are comparatively small in relation to the circular arc sections defined by the guide elements. At least 80% of the entire circumference in the region of the claws 18 as well as of the guide elements 45 is therefore formed by the elements 44, 45. As can be seen in particular in FIGS. 18 and 19, the claws 18 each comprise at their end a (radially inwardly directed) projection 46. Said projection is driven against the ampoule (not shown) such that said ampoule breaks. This can also be seen from FIGS. 20 and 21.

Figure 18:
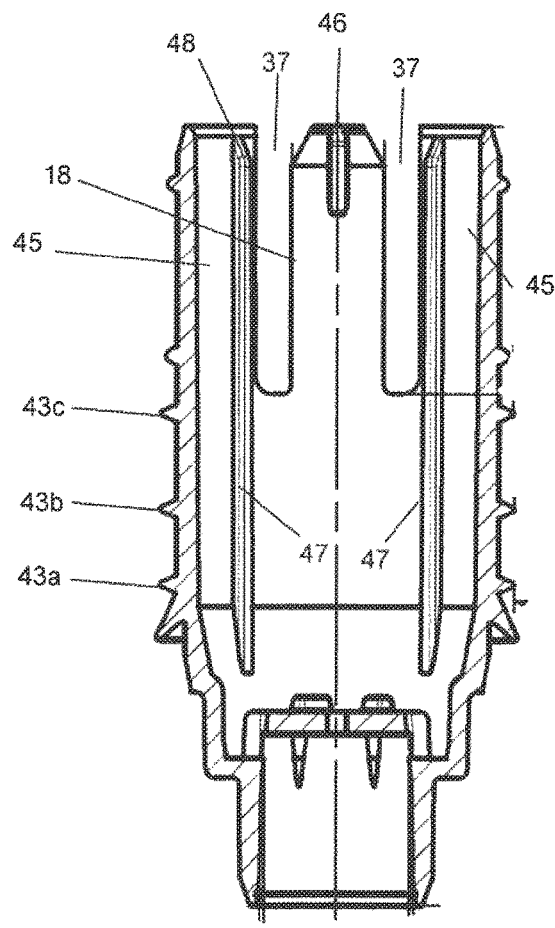
FIG. 18 shows a section along the line XVIII-XVIII in FIG. 17.
Figure 19:
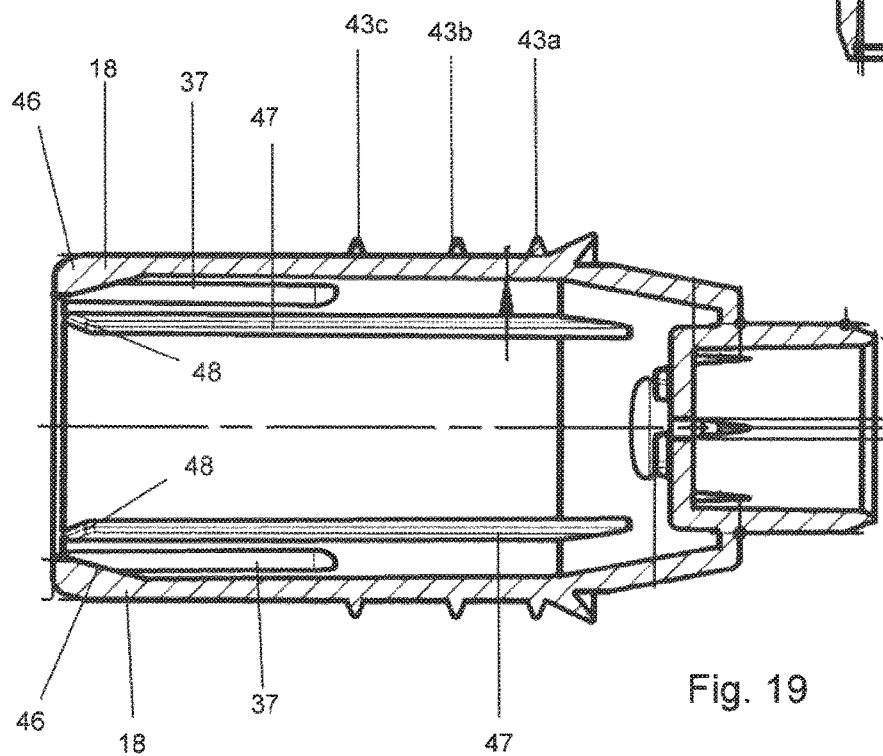
FIG. 19 shows a section along the line XVIIII-XVIIII.

In particular, FIGS. 18 and 19 additionally show axially extending ribs 47, one each of which is arranged on an inner peripheral surface of an associated guide element 45. The ampoule is able to be reliably positioned by means of said ribs such that controlled and defined breaking is made possible. Ends 48 of the ribs 47 which come into contact with the ampoule (not shown) first are realized in order to position the ampoule in a reliable manner.

Figure 17:
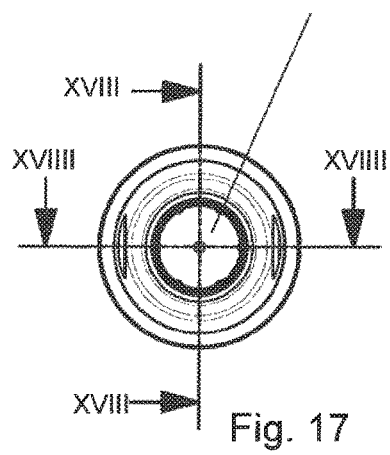
FIG. 17 shows a front view of the head part according to FIG. 16.
Figure 20:
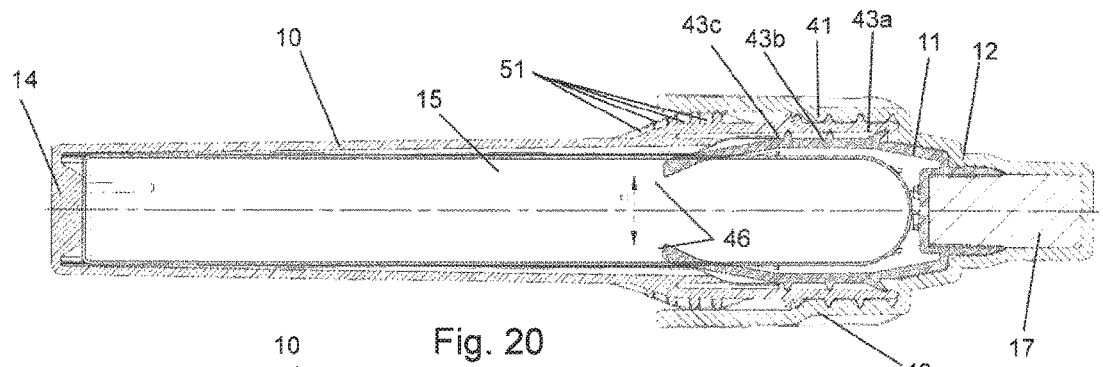
FIG. 20 shows a sectional view of an alternative embodiment of the applicator pen with a head part according to FIG. 17 in a first position.
Figure 21:
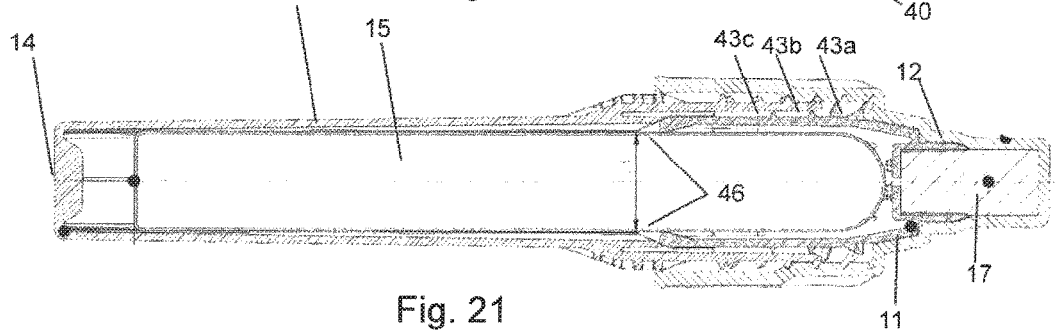
FIG. 21 shows a section analogous to FIG. 20 in a second position.

FIGS. 20 and 21 show sectional views of an embodiment of the applicator pen with a head part according to FIGS. 17 to 19. FIG. 21, in this case, shows the state prior to breaking the ampoule 15. FIG. 20 shows a state after breaking the ampoule 15. The position according to FIG. 20 is realized, proceeding from the position according to FIG. 21, by a screw movement analogous to the embodiment according to FIGS. 14 and 15 (see above). In this respect, threads 40, 41 corresponding to the embodiment according to FIGS. 14 and 15 are also provided here. As an alternative to this, a (purely) translatory movement of the head part can also be made possible.

As can additionally be seen in particular in FIG. 16, the guide elements 45 comprise part ring portions 49 which are arranged on an outer peripheral surface and form a further barrier against a passage of liquid.

Proceeding from FIG. 21, the head part is moved in the direction of the rear end until it reaches the end position according to FIG. 20. As can be seen in FIG. 21, the sealing rings 43b, 43c are already in contact with the base part 10. On account of the notches provided in the sealing rings 43b, 43c (cf. FIG. 16), air is able to flow through the notches 44 such that overpressure, which is a result of the head part, before it has reached the position in FIG. 21, already having covered a certain distance such that an inner volume of the applicator pen has become smaller, is able to be reduced. On the other hand, the notches 44 are also dimensioned such that a (small) overpressure remains which is desirable with regard to the filling of the applicator-part. If the head part is then moved further until it reaches the position in FIG. 20, the sealing ring 43a is also in contact with the base part 10 (the sealing ring 43a can be seen in detail in FIGS. 18 and 19). As the sealing ring 43a does not comprise interruptions (notches), a sealed closure between the head part and the base part is consequently realized.

Figure 22:
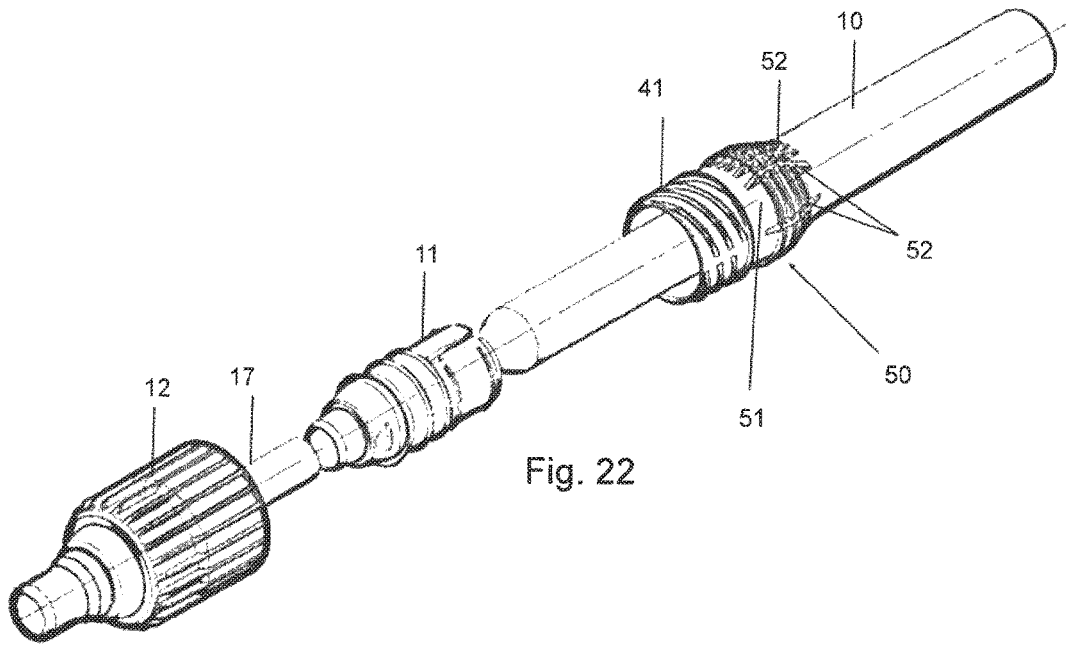
FIG. 22 shows an oblique view (in part in an exploded view) of the applicator pen according FIGS. 20 and 21.

The base part 10 (cf. FIG. 22 and FIGS. 20 and 21) comprises a cruciform structure 50. The cruciform structure 50 includes several (specifically four) peripheral rings 51. Said rings additionally prevent (in part) liquid escaping. In addition, the rings 51 improve the grip of the base part, therefore fulfill a dual function such that material is able to be saved overall. In addition, the crosshead nut 50 includes axially extending ribs 52 which cross the rings 51. Ends of the ribs 52 are chamfered. On the one hand, this facilitates sliding on the cap 12 and, on the other hand, gripping the base part 10. The ribs 52 therefore also have a "dual function" and allow further material to be saved. The ribs 52 do not necessarily have to be chamfered at their ends (for example they can be chamfered at just the one end or only at the other end or not at all). The rings 51 are preferably not arranged at the same height in relation to a center axis (as can be seen in FIGS. 20 and 21), but, at an increasing height when viewed from the rear end 14 of the applicator pen. They can also all be arranged at the same height. The rings 51 can also be provided without ribs 52 or vice versa (the ribs 52 can be provided without rings 51). A cruciform structure 50, therefore, does not necessarily have to be realized.

LIST OF REFERENCES

3 Hollow body
10 Base body
11 Head part (movable portion)
12 Closure cap
13 Outlet region
14 Rear end
15 Ampoule
16 Sponge
17 Liquid-applicator felt
18 Claw
19 Stop
20 Stop
21 Arrow
22 End
23 Run-up inclination
24 Run-up inclination
25 Slot
26 Sealing ring
27 Screw thread
28 Cone portion
29 Cone portion
30 Annular slanting surface
31 Annular slanting surface
32 Recess
33a-33c Sealing ring
34 Annular groove
35 Ring-shaped constriction
36 Peripheral surface
37 Slot
38a, 38b Sealing ring
39 Annular groove
40 Thread of the cap 12
41 Thread of the base body 10
42 Positioning journals
43,43a, 43b,43c Sealing rings or sealing lips
44 Notch
45 Guide element
46 Projection
47 Ribs
48 Part-ring portions
50 Cruciform structure
51 Ring
52 Rib

The invention claimed is:

1. An applicator pen for discharging a liquid onto a surface, said applicator pen including a hollow body and an ampoule received in the hollow body, including a peripheral surface, for receiving the liquid, wherein the ampoule is able to be broken to enable the liquid to escape,
wherein a breakage device is provided with an axially movable portion and is realized in such a manner that a movement of the movable portion in the axial direction results in the breaking of the ampoule, the breakage device including at least one claw in such a manner that the claw is driven against the peripheral surface of the ampoule by the axial movement of the movable portion, and
a rotatable portion is provided in such a manner that a rotation of the rotatable portion drives the movable portion in the axial direction such that the ampoule breaks.

2. The applicator pen as claimed in claim 1,
wherein the breakage device includes a diverting device in such a manner that a force, which acts axially on account of the movement of the movable portion, is diverted in the direction of the peripheral surface of the ampoule.

3. The applicator pen as claimed in claim 1,
wherein the hollow body includes a head part as well as a base body, wherein the base body includes an end of the applicator pen which is remote from an outlet region.

4. The applicator pen as claimed in claim 3,
wherein the head part includes a plastics material end piece with a narrow slot for discharging the liquid.

5. The applicator pen as claimed in claim 3,
wherein the head part comprises at least one porous liquid absorption body for applying the liquid onto the surface.

6. The applicator pen as claimed in claim 1,
wherein the hollow body comprises at least one run-up inclination in such a manner that an axially acting force is converted into a radially inwardly directed force.

7. The applicator pen as claimed in claim 1, wherein the hollow body comprises at least two parts,
wherein at least one sealing ring is provided on at least one surface of one of the parts which faces a surface of a further part.

8. The applicator pen as claimed in claim 7,
wherein part of the hollow body is a base body, including an end of the applicator pen remote from an outlet region, and/or
part of the hollow body is a head part which adjoins the base body, and/or
part of the hollow body is a closure cap as the rotatable portion.

9. The applicator pen as claimed in claim 1, comprising a closure cap as the rotatable portion for closing the hollow body.

10. The applicator pen as claimed in claim 1,
wherein a removable film element is arranged around the applicator pen.

11. An applicator pen for discharging a liquid onto a surface, said applicator pen including a hollow body and an ampoule received in the hollow body, including a peripheral surface, for receiving the liquid, wherein the ampoule is able to be broken to enable the liquid to escape,
wherein a breakage device is provided with an axially movable portion and is realized in such a manner that a movement of the movable portion in the axial direction results in the breaking of the ampoule,
the hollow body comprises at least two parts,
at least one sealing ring is provided on at least one surface of one of the parts which faces a surface of a further part, and
the at least one sealing ring comprises at least one interruption.

* * * * *